United States Patent
Imhof

(10) Patent No.: US 6,439,028 B1
(45) Date of Patent: Aug. 27, 2002

(54) METHOD AND EQUIPMENT FOR MEASURING VAPOR FLUX FROM SURFACES

(75) Inventor: Robert E. Imhof, Kent (GB)

(73) Assignee: South Bank University Enterprises Limited, London (GB)

( * ) Notice: Subject to any disclaimer, the term of this patent is extended or adjusted under 35 U.S.C. 154(b) by 0 days.

(21) Appl. No.: 09/743,619

(22) PCT Filed: Jul. 8, 1999

(86) PCT No.: PCT/GB99/02183
§ 371 (c)(1),
(2), (4) Date: Feb. 15, 2001

(87) PCT Pub. No.: WO00/03208
PCT Pub. Date: Jan. 20, 2000

(30) Foreign Application Priority Data

Jul. 10, 1998 (GB) ................................................ 9814862

(51) Int. Cl.⁷ ........................ G01N 13/04; G01N 25/58; G01N 15/08

(52) U.S. Cl. .................... 73/29.01; 73/24.04; 73/25.04; 73/76

(58) Field of Search ........................... 73/29.01, 335.04, 73/335.05, 24.04, 25.04, 73, 76

(56) References Cited

U.S. PATENT DOCUMENTS

| | | | | |
|---|---|---|---|---|
| 3,444,092 A | * | 5/1969 | Truhan | 252/359 |
| 3,521,865 A | * | 7/1970 | Kertzman | 261/95 |
| 4,050,995 A | * | 9/1977 | Bredeweg | 204/1 T |
| 4,787,052 A | * | 11/1988 | Yamaguchi | 364/550 |
| 5,344,622 A | * | 9/1994 | Faddis et al. | 422/306 |
| 5,752,411 A | | 5/1998 | Harpster | 73/861.04 |
| 5,826,458 A | * | 10/1998 | Little | 73/73 |
| 5,847,263 A | * | 12/1998 | Springmann et al. | 73/29.01 |
| 5,907,091 A | * | 5/1999 | Pause | 73/38 |
| 5,957,380 A | * | 9/1999 | Fitterman et al. | 239/55 |
| 6,073,479 A | * | 6/2000 | Shapiro et al. | 73/29.01 |

FOREIGN PATENT DOCUMENTS

| | | | | |
|---|---|---|---|---|
| DE | G8700749.5 | 1/1987 | | G01N/25/56 |
| GB | 1532419 | 11/1978 | | G01N/7/14 |

\* cited by examiner

Primary Examiner—Daniel S. Larkin
Assistant Examiner—David J. Wiggins
(74) Attorney, Agent, or Firm—Ronald B. Sherer; Bartlett & Sherer

(57) ABSTRACT

A method and equipment for measuring vapor flux from a surface e.g. the rate of water loss from human skin which is useful in the evaluation of the efficiency of the skin/water barrier uses a closed cylinder which is placed with the open end against the skin and the closed end is cooled. By measuring the temperature and relative humidity within the cylinder the water vapor flux can be determined.

42 Claims, 1 Drawing Sheet

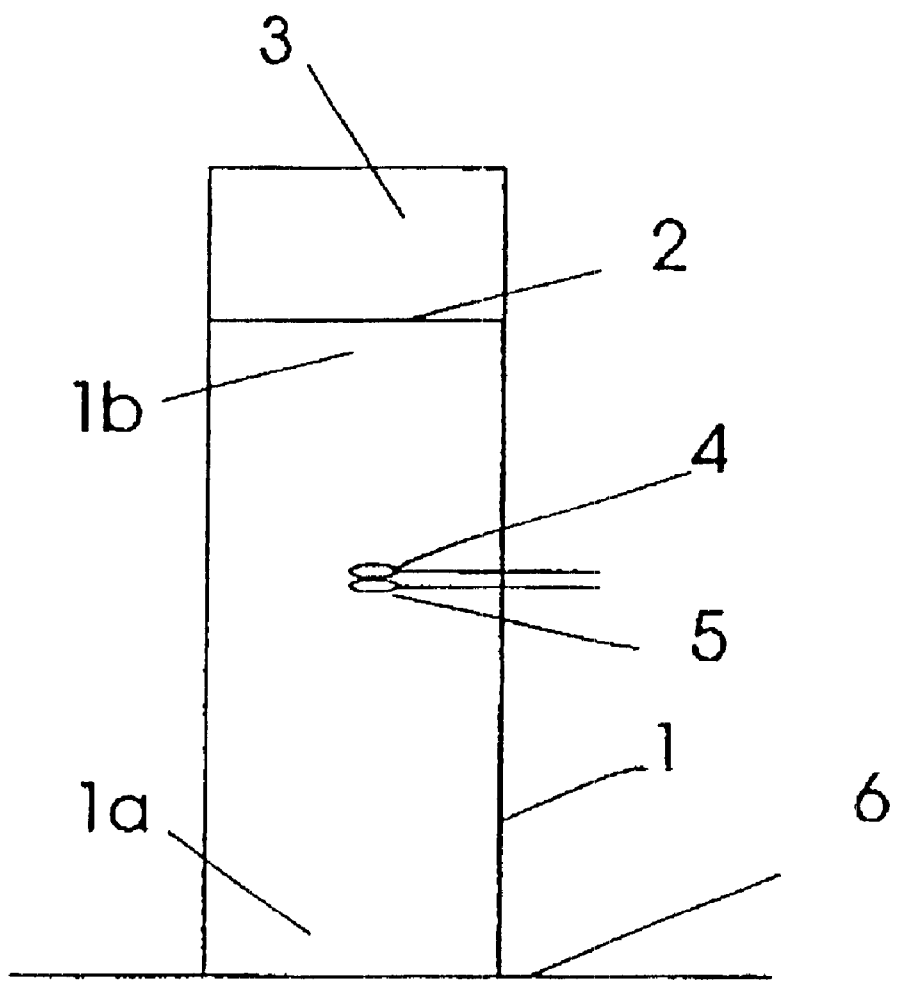

METHOD AND EQUIPMENT FOR MEASURING VAPOR FLUX FROM SURFACES

The present invention relates to a method and a device for measuring vapour flux from a surface, more particularly it relates to a method and a device which can be used to measure the rate of water loss from human skin.

The transepidermal water loss (TEWL) is important in the evaluation of the efficiency of the skin/water barrier. Damage to the skin resulting from various skin diseases, burns and other damage can affect the TEWL and measurement of the TEWL can indicate such damage and possibly its early onset or response to treatment. It therefore has use in clinical diagnosis.

As the TEWL is a measure of the effectiveness of the skin/water barrier its measurement is important in prematurely born infants, when dehydration due to excessive water loss can have serious adverse results. The TEWL, is also used in testing the effect of pharmaceutical and cosmetic products applied to the skin.

GB patent 1532419 describes an instrument for measuring the rate of water loss from the skin in which an open cylinder containing two spaced apart relative humidity sensors and two temperature sensors is placed on the skin so that water vapour escaping from the skin diffuses along the cylinder and passes the sensors. The output from these sensors can be used to measure the concentration gradient of water vapour in the cylinder and hence the water vapour flux from the skin.

However this instrument can only function accurately in a homogeneous diffusion zone which means that the air inside the cylinder must be still. In practice, air currents and other air movements in the vicinity of the open end of the cylinder affect the measurements and introduce errors. Other errors are associated with changes of ambient humidity.

We have now devised equipment and a method for measuring the water vapour flux from a surface which reduces these problems.

According to the invention there is provided equipment for measuring the water vapour flux from a surface which comprises a cylinder with an opening at one end, which opening is adapted to be placed against the surface of interest, the other end of the cylinder being closed by means of a cooled surface; the cylinder containing sensors, which sensors being able to measure quantities, such as relative humidity and temperature, from which the flux of water vapour from the surface of interest can be calculated.

The invention also provides a method for measuring the water vapour flux from a surface, which method comprises enclosing a zone adjacent to the surface of interest within a cylinder which is open at one end and closed at the other end, by placing the open end of the cylinder against the surface of interest, cooling the surface closing the closed end of the cylinder and measuring quantities, such as relative humidity and temperature within the cylinder, from which the flux of water vapour forms the surface of interest can be calculated.

The closed surface is preferably cooled to a temperature at which the water vapour in its vicinity condenses to liquid water or ice and steady conditions of water vapour diffusion are established within the cylinder with the concentration of water vapour in the immediate vicinity of the cold surface being lower than in the immediate vicinity of the surface of interest. By this means, a water vapour concentration gradient is established alone the length of the cylinder.

Given a suitable geometrical arrangement of sensors, their readings of typically relative humidity and temperature can be used to calculate the water vapour concentration gradient along tete length of the cylinder. The relationship between the water vapour flux and the water vapour concentration gradient along the length of the cylinder is well known, for example it is explained in GB 1532419.

Various methods of measuring the water vapour concentration gradient along the length of the cylinder exist. In one implementation, the concentration of water vapour at a known distance from the cooled surface is measured and, using the known concentration of water vapour in the immediate vicinity of the cooled surface, the gradient of water vapour concentration along the length of the cylinder can the calculated.

The concentration of water vapour can be measured by measuring the relative humidity, in which case there is preferably a second sensor which is able to measure the temperature substantially at the location of the sensor which measures the relative humidity. From measurements of the relative humidity and associated temperature, the concentration of water vapour at the sensor location can be determined.

A suitable and convenient choice of relative humidity sensor includes sensors based on the change in capacitance or change in electrical conductivity etc., which are widely commercially available. A suitable and convenient choice Of temperature sensor includes the conventional thermocouple and thermistor, which are widely commercially available. Alternatively a composite sensor can be used which simultaneously measures the relative humidity and the temperature so that one such composite sensor can produce the required signals.

Preferably the sensors take their measurements at a point or in a plane substantially parallel to the surface of interest, in order to make the measurement of water vapour flux more accurate.

An additional temperature sensor is preferably placed in contact with tile cold surface in order both to maintain its temperature at a constant value and to provide a temperature reading from which the concentration of water vapour in its immediate vicinity can be calculated.

Preferably the outputs from the sensors are fed to a processing device such as a microprocessor or PC, which is programmed to convert the signals from the sensors to the required type of output or readout. By this means a user of the equipment can obtain a result in a form which requires little further processing and can be interpreted easily e.g. the flux of water vapour can be directly displayed.

The closed surface of the cylinder can be cooled by conventional cooling means and preferably uses an electrical cooling means e.g. one based on the Peltier effect. This enables the cooling to be accurately controlled at the requisite level quickly and easily.

The water which is condensed at the cold surface can be re-evaporated by heating the surface during times when the instrument is not being used for measurement. If tile cooler is a Peltier device, then this can conveniently be accomplished by reversing the current flow through it.

The cylinder is the common geometry of measurement chamber for such instruments, but any convenient shape can be used e.g. rectangular parallelepiped, prism, etc. The measurement chamber is preferably made of compact size so that it occupies a small area and can easily be placed on the surface of interest, e.g. the skin at the desired location of a TEWL measurement. The measurement chamber can conveniently be constructed in the form of a wand or with a convenient handle etc.

The equipment and method can be used to measure any vapour flux from a surface although, when the vapour is not water vapour, the sensor and cold plate temperature are chosen accordingly.

The equipment can be used with any surface and apart from skin the equipment can be used to measure water vapour flux from plants, etc.

In use, the open end of the cylinder is placed against the skin and the closed end of the cylinder is cooled and readings from the sensors are fed to a processor which converts these readings to the desired water flux measure. After a short period to allow the measurement conditions to stabilise, readings are taken. Alternatively, readiness can be taken continuously or periodically in order to record the time change of the signals and the water vapour flux calculated according to suitable criteria.

Unlike existing equipment, which is open to the atmosphere to allow the water vapour flux to escape, the closed cylinder means that neither air movement nor humidity in the air outside the cylinder can affect the measurements taken and so more accurate readings are obtained.

In the implementation described, only one relative humidity sensor and two temperature sensors are required, thus simplifying the construction. This does not preclude the use of more sensors, however. If relative humidity and associated temperature are sensed at two locations within the cylinder, as with conventional embodiments of such instruments, then the gradient of water vapour concentration can be calculated without requiring a knowledge of the water vapour concentration in the immediate vicinity of the cold surface. The use of additional sensors would allow more precise calculations of water vapour flux to be performed. It may also be convenient to incorporate additional sensors in the equipment, e.g. to measure ambient temperature, skin temperature, etc.

An alternative means of measuring water vapour flux is to measure the mass of water condensed on the cold surface of the cylinder, the mass of water per unit interval of time being numerically equal to the flux of water vapour emanating from the surface of interest. A convenient mass sensor, such as a quartz microbalance, can therefore be used in place of the relative humidity sensor(s) in an alternative implementation of the device.

An alternative means of measuring water vapour concentration in the cylinder includes a sensor based on measuring the absorption of infrared radiation of suitable wavelength by the water vapour.

The invention is described with reference to the accompanying drawing which is a side view of an embodiment of equipment according to the invention.

In the drawing a chamber in the from of cylinder (1) is open at end (1a) and is closed at the end (1b) by a surface (2) which is in contact with a Peltier cooling device (3). Inside the cylinder (1) is a capacitive relative humidity sensor (4) and a thermocouple (5) which measures the temperature at the location of the relative humidify sensor (4). An additional thermocouple (7) is placed in contact with the cooled surface (2). The outputs of (4), (5) and (7) are fed to a computer (not shown).

To measure the water vapour flux from the skin (6) of a person, the open end (1a) is placed against the skin as shown and the surface (2) is cooled down to a sufficiently low temperature to maintain a substantially lower water vapour pressure in its immediate vicinity than in the immediate vicinity of skin at the other end of the cylinder.

The computer is programmed with a program so that the output from the sensors (4), (5) and (7) are converted to a reading in the desired form, e.g. water vapour flux from the surface.

After a short period of time (to allow for steady state conditions to he attained inside cylinder (1)), the readings are evaluated by the computer. Alternatively, readings can be taken continuously or periodically in order to record the time change of the signals and the water vapour flux calculated according to suitable criteria.

After the measurement or periodically, when convenient, the cold surface is heated to re-evaporate condensate, thus preventing a build-up of condensate (liquid water or ice).

What is claimed is:

1. Equipment for measuring a water vapour flux from a surface which comprises a cylinder with a first end which is open and a second end which is closed, the first end being adapted to be placed against said surface and there being a cooling means adapted to cool the second end of said cylinder to form a cold cylinder end; the cylinder containing one or more sensors which are able to measure a plurality of quantities from which the flux of water vapour from said surface can be calculated.

2. Equipment as charmed in claim 1 in which the said sensors are able to measure relative humidity and temperature.

3. Equipment as claimed in claim 2 in which there is first sensor able to measure the relative humidity and a second sensor which is able to measure the temperature substantially at the location of the first sensor.

4. Equipment as claimed in claim 2 in which the sensor for measuring relative humidity is based on the charge in capacitance or change in electrical conductivity.

5. Equipment as claimed in claim 2 in which the sensor for measuring relative humidity is based on the change in capacitance or change in electrical conductivity.

6. Equipment as claimed in claim 1 in which said sensor(s) comprise means for measuring the mass of water condensed on the cold end of the cylinder.

7. Equipment as claimed in claim 1 in which the sensor(s) comprise a quartz microbalance.

8. Equipment as claimed in claim 1 in which the sensor which is able to measure quantities from which the flux of water vapour from the surface can be calculated is a sensor based on measuring the absorption of infrared radiation of suitable wavelength by the water vapour.

9. Equipment as claimed in claim 2 in which the sensor for measuring the temperature is a thermocouple or a thermistor.

10. Equipment as claimed in claim 3 in which the sensor for measuring the temperature is a thermocouple or a thermistor.

11. Equipment as claimed in claim 6 in which the sensor for measuring the temperature is a thermocouple or a thermistor.

12. Equipment as claimed in claim 8 in which the sensor for measuring the temperature is a thermocouple or a thermistor.

13. Equipment as claimed in claim 1 in which the sensor which is able to measure quantities from which the flux of water vapour from the surface can be calculated is a composite sensor which simultaneously measures the relative humidity and the temperature.

14. Equipment as claimed in claim 1 in which the sensor or sensors are positioned so as to take their measurements at a point or in a plane substantially parallel to the surface.

15. Equipment as claimed in claim 2 in which the sensor or sensors are positioned so as to take their measurements at a point or in a plane substantially parallel to the surface.

16. Equipment as claimed in claim 8 in which the sensor or sensors are positioned so as to take their measurements at a point or in a plane substantially parallel to the surface.

17. Equipment as claimed in claim 1 in which there is an additional temperature sensor is adapted to be placed in contact with the second end of the cylinder.

18. Equipment as claimed in claim 8 in which the outputs from the sensors are fed to a processing device.

19. Equipment as claimed in claim 13 in which the cooling means is based on the Peitier effect.

20. Equipment as claimed in claim 6 in which the cooling means is based on the Peltier effect.

21. Equipment as claimed in claim 8 in which the cooling means is based on the Peltier effect.

22. Equipment as claimed in claim 14 in which the cooling means is based on the Peltier effect.

23. Equipment as claimed in claim 17 in which the cooling means is based on the Peltier effect.

24. A method for measuring a water vapour flux from a surface, which method comprises enclosing a zone adjacent to the surface within a cylinder which at one end and closed at the other end, by placing the open end of the cylinder against the surface, cooling the closed end of the cylinder to form a cold end and measuring a plurality of quantities from which the flux of water vapour from the surface of interest can be calculated.

25. A method as claimed in claim 24 in which the closed end of the cylinder is cooled to a temperature at which the water vapour in its vicinity condenses to liquid water or ice and steady conditions of water vapour diffusion are established within the cylinder, with the concentration of water vapour in the immediate vicinity of the cold end of the cylinder being lower than in the immediate vicinity of the surface.

26. A method as claimed in claim 24 in which the concentration of water vapour at a known distance from the cooled end of the cylinder is measured and, using the known concentration of water vapour in the immediate vicinity of the cooled end, the gradient of water vapour concentration along the length of the cylinder calculated.

27. A method as claimed in claim 25 in which the concentration of water vapour at a known distance from the cooled end of the cylinder is measured and, using the known concentration of water vapour in the immediate vicinity of the cooled end, the gradient of water vapour concentration along the length of the cylinder calculated.

28. A method as claimed in claim 24 in which the concentration of water vapour is measured by measuring the relative humidity and the temperature at simultaneously at the same location.

29. A method as claimed in claim 25 in which the concentration of water vapour is measured by measuring the relative humidity and the temperature at simultaneously at the same location.

30. A method as claimed in claim 26 in which the concentration of water vapour is measured by measuring the relative humidity and the temperature at simultaneously at the same location.

31. A method as claimed in claim 24 in which the relative humidity is measured by a sensor which measures the change in capacitance or change in electrical conductivity.

32. A method as claimed in claim 24 in which the temperature is measured by means of thermocouple and thermistor.

33. A method as claimed in claim 24 in which the sensor or sensors take their measurements at a point or in a plane substantially parallel to the surface.

34. A method as claimed in claim 24 in which the concentration of water vapour is measured by measuring the relative humidity and the temperature at simultaneously at the same location.

35. A method as claimed in claim 24 in which the concentration of water vapour is measured by measuring the relative humidity and the temperature at simultaneously the same location.

36. A method as claimed in claim 24 in which there is a temperature control means placed in contact with the cold end of the cylinder to maintain its temperature at a constant value and from which temperature the concentration of water vapour in its immediate vicinity is calculated.

37. A method as claimed in claim 24 in which the outputs from the sensors are fed to a processing device which is programmed to convert the signals from the sensors to the required type of output or readout.

38. A method as claimed in claim 24 in which the outputs from the sensors are fed to a processing device which is programmed to convert the signals from the sensors to the required type of output or readout.

39. A method as claimed in claim 33 in which the outputs from the sensors are fed to a processing device which is programmed to convert the signals from the sensors to the required type of output or readout.

40. A method as claimed in claim 24 in which the closed end of the cylinder is cooled by a cooling means based on the Peltier effect.

41. A method as claimed in claim 24 in which the water which is condensed at the cold end of the cylinder is re-evaporated by heating said cold end.

42. A method as claimed in claim 41 in which said cold end of the cylinder is both heated and cooled by means based on the Peltier effect.

* * * * *